(12) United States Patent
Gonzalez Bayon et al.

(10) Patent No.: US 10,309,570 B2
(45) Date of Patent: Jun. 4, 2019

(54) CONNECTION DEVICE, PIPES INCORPORATING SAME FOR FLUID TRANSMISSION PIPING OF AN AIRCRAFT OR A SPACECRAFT, AND METHOD FOR MANUFACTURING SAID DEVICE

(71) Applicant: HUTCHINSON, Paris (FR)

(72) Inventors: Cristina Gonzalez Bayon, Amilly (FR); Stéphane Bergere, Saint Jean le Blanc (FR); Bertrand Florentz, Paucourt (FR)

(73) Assignee: HUTCHINSON, Paris (FR)

( * ) Notice: Subject to any disclaimer, the term of this patent is extended or adjusted under 35 U.S.C. 154(b) by 210 days.

(21) Appl. No.: 15/033,716

(22) PCT Filed: Nov. 6, 2013

(86) PCT No.: PCT/FR2013/052649
§ 371 (c)(1),
(2) Date: May 2, 2016

(87) PCT Pub. No.: WO2015/067859
PCT Pub. Date: May 14, 2015

(65) Prior Publication Data
US 2016/0273696 A1    Sep. 22, 2016

(51) Int. Cl.
*F16L 43/00* (2006.01)
*F16L 57/00* (2006.01)
(Continued)

(52) U.S. Cl.
CPC .......... *F16L 43/008* (2013.01); *A45D 34/042* (2013.01); *A61K 8/891* (2013.01);
(Continued)

(58) Field of Classification Search
CPC ....... F16L 27/125; F16L 27/12; F16L 43/008; F16L 43/02; F16L 43/00
(Continued)

(56) References Cited

U.S. PATENT DOCUMENTS 6,125,891 A    10/2000  Witmer et al.
6,499,770 B1 *  12/2002  Glista ................. F16L 27/0808
                                                285/223
(Continued)

FOREIGN PATENT DOCUMENTS

EP    0 058 783 A1    9/1982
EP    1 243 841 A1    9/2002
WO    2009/124910 A1  10/2009

OTHER PUBLICATIONS

International Search Report dated Sep. 5, 2014, issued in corresponding International Application No. PCT/FR2013/052649, filed Nov. 6, 2013, 5 pages.
(Continued)

*Primary Examiner* — Aaron M Dunwoody
(74) *Attorney, Agent, or Firm* — Christensen O'Connor Johnson Kindness PLLC (57) ABSTRACT

A connection device is suitable for connecting two tubes to one another, and optionally to a fluid tank for fluid transmission piping of an aircraft or a spacecraft Also disclosed are pipes incorporating said tubes and said device; and a method for manufacturing said device. The device includes an injection-molded tip that has at least one angled or inwardly curved area and is made of a composite material with a thermoplastic matrix reinforced by a reinforcement system including carbon fibers. The tip has a median longitudinal mold parting plane (P). The carbon fibers extend so as to be oriented along the tip, which incorporates mechanical and vibratory stiffening means which are integrally molded with the tip and lie in said parting plane or sym- (Continued)

metrically relative to said plane in said at least one area and/or immediately near said area.

16 Claims, 3 Drawing Sheets

(51) Int. Cl.
| | |
|---|---|
| *A45D 34/04* | (2006.01) |
| *A61K 8/891* | (2006.01) |
| *A61K 8/895* | (2006.01) |
| *A61K 8/92* | (2006.01) |
| *A61Q 1/04* | (2006.01) |
| *C08G 77/442* | (2006.01) |
| *C08L 83/10* | (2006.01) |

(52) U.S. Cl.
CPC ............... *A61K 8/895* (2013.01); *A61K 8/92* (2013.01); *A61Q 1/04* (2013.01); *C08G 77/442* (2013.01); *C08L 83/10* (2013.01); *F16L 57/00* (2013.01); *A45D 34/045* (2013.01); *A45D 2200/055* (2013.01); *A45D 2200/1018* (2013.01); *A61K 2800/544* (2013.01); *A61K 2800/87* (2013.01)

(58) Field of Classification Search
USPC ........................................ 285/298, 223, 179
See application file for complete search history.

(56) References Cited

U.S. PATENT DOCUMENTS

| | | | | |
|---|---|---|---|---|
| 8,172,272 | B2* | 5/2012 | Petit ..................... | F16L 39/005 |
| | | | | 285/123.12 |
| 8,562,027 | B2* | 10/2013 | Barre .................... | F16L 25/01 |
| | | | | 285/223 |
| 2004/0016467 | A1* | 1/2004 | Blackmore ........... | F16L 55/179 |
| | | | | 138/99 |
| 2008/0078880 | A1* | 4/2008 | Petit ...................... | F16L 21/03 |
| | | | | 244/135 R |
| 2009/0079186 | A1* | 3/2009 | Frost .................... | F16L 27/026 |
| | | | | 285/236 |
| 2010/0116941 | A1* | 5/2010 | Ciolcyzk ................ | F16L 9/125 |
| | | | | 244/135 R |
| 2012/0132755 | A1* | 5/2012 | Petit ....................... | B64C 3/187 |
| | | | | 244/131 |
| 2013/0220474 | A1* | 8/2013 | Sheridan ................ | B32B 27/00 |
| | | | | 138/174 |

OTHER PUBLICATIONS

Written Opinion of the International Searching Authority dated Sep. 5, 2014, issued in corresponding International Application No. PCT/FR2013/052649, filed Nov. 6, 2013, 5 pages.
International Preliminary Report on Patentability dated May 10, 2016, issued in corresponding International Application No. PCT/FR2013/052649, filed Nov. 6, 2013, 1 page.

* cited by examiner

CONNECTION DEVICE, PIPES INCORPORATING SAME FOR FLUID TRANSMISSION PIPING OF AN AIRCRAFT OR A SPACECRAFT, AND METHOD FOR MANUFACTURING SAID DEVICE

CROSS-REFERENCE TO RELATED APPLICATION

This application is a National Stage of WOSN PCT/FR2013/052649, filed Nov. 6, 2013.

FIELD OF THE INVENTION

The present invention relates to a connection device between two tubes, and optionally furthermore to a fluid tank for transmission piping of this fluid in an aircraft or a spacecraft, pipes for such a piping incorporating these tubes and this connection device connecting them to one another, and method for manufacturing this device. The invention in particular applies to piping of a fuel circuit of a civilian or military aircraft, in particular equipped with composite wings, having specified that it generally relates to connections and fastenings of all fluid transfer tubes, for example for fuel, water production, wastewater discharge, drainage, oxygen or cooling circuits, non-limitingly.

BACKGROUND OF THE INVENTION

Document WO-A1-2011/007100 discloses connecting devices between metal tubes intended to protect an aircraft fuel piping from lightning. These devices include plastic connectors and metal connectors connecting the tubes to one another, having specified that the plastic connectors include a radially outer enclosure with two tips surrounding an inner tip, and are made from an injected composite material with a base of a thermoplastic matrix reinforced by discontinuous fibers with a length for example comprised between 3 and 5 mm. O-rings made from electrically insulating elastomer provide a tight connection between these connectors and the tubes that they connect to one another.

SUMMARY

The fuel pipes or lines of current aircraft are usually made from aluminum, like the wings in which they are housed. In the last few years, however, wings and fuel pipes have begun to be designed in composite materials, in order to lighten these pipes and the airfoil incorporating them as much as possible.

Aside from these mass savings, an effort has been made to control the electrical conductivity of the entire airfoil in case of lightning strike, while eliminating electrostatic charges within these pipings. Indeed, it is necessary to ensure, during a lightning strike, that on the one hand the lightning flows primarily through the structures of the wings, and on the other hand the accumulation of electrostatic charges inside the piping traveled through by the fuel is strictly limited to avoid any risk of explosion by inflammation of the fuel.

In the past, the connecting tips or connectors that make it possible on the one hand to connect composite tubes of the fuel piping to one another and on the other hand to fasten these tubes to the structure of the fuel tank using a flange provided with fastening lugs equipping these tips, were typically made from aluminum foundry. The constraints related to weight reduction, in order to reduce consumption and emissions, today are leading to lightening these connectors by transitioning them to machined, anodized and slip-treated aluminum, as explained below.

To allow the relative movements and operating deformations (for example, due to expansions) between the structures and these tubes and connectors, the cylindrical link between the connector and each tube must be both sliding and rolling and it must have a low roughness to facilitate this sliding, thus reducing the assembly forces, the loads transmitted to the structures during operation and the wear of the joints, which makes it possible to avoid the appearance of leaks by abrasion over time within the pipes.

To that end, the cylindrical links of the current connectors are machined, then coated with slippery materials (e.g., lubricants, for example of the Molycote® type, deposited by spraying, then hot cross-linked), since the aluminum is not slippery enough. Such metal connectors are present on many types of aeronautic circuits in addition to fuel circuits, such as water supply, wastewater discharge, cooling, drainage, etc. circuits.

One major drawback of these known cylindrical links is that the slippery coatings deposited on the machined connectors cause the connecting surfaces not to be electrically conductive.

Yet in light of the aforementioned priority constraint, which requires continuously improving the safety of airplanes, in particular for their fuel circuits housed in wings made from composite materials, it is necessary to look for new solutions that are both insulating enough to minimize explosion risks by lightning strike, and "dissipative" to discharge these electrostatic charges.

A second major constraint today consists of decreasing the weight and manufacturing cost of airplanes.

Owing to the aforementioned change to the manufacturing method for the aluminum-based metal connectors replacing molten aluminum with machined, anodized and slip-treated aluminum, major weight reductions were possible. Indeed, the performance of new "UGV" machining means combined with the greatly improved mechanical characteristics of alloys machined in the mass relative to molded aluminums, make it possible to reduce the wall thicknesses to minimal values of 1 mm, which are technological minimums for machining (at lower thicknesses, the cutting force deforms the walls), or a surface density of about 2.7 kg/m$^2$.

These machined and treated connectors are highly electrically conductive in their mass. However, the tendency toward corrosion of the aluminum requires protecting these connectors using surface treatments, for example of the Chromic Anodic Oxidation (CAO) type and also in the stepped zones of the sealing gaskets by slippery surface treatments which, as explained above, do not conduct the current.

That is why additional electrically conductive braids are used on the one hand connecting the tubes to the connectors, and on the other hand connecting these connectors to the structure of the tank to obtain the electrical conductivity necessary to guarantee the electrostatic discharge of the fuel pipes and thus avoid explosion risks of the fuel tank by accumulation of electrostatic charges.

One major drawback of these conductive braids is that they extend the assembly time, increase the risks of incorrect assembly, and raise the overall manufacturing and assembly costs and the weight of the pipes.

With the arrival of composite wings and the risk of lightning preferably passing through the fuel pipes, these machined and treated aluminum connectors, even though their surfaces are insulating, have excessively high electrical conductivity in their mass to prevent any passage of lightning in the piping. The current solution consists of producing "lightning-breaks" by incorporating electrically insulating tubings, called "insulators", in the piping. Today, these insulators are typically made from wound tubular structures of insulating glass fibers.

One major drawback of these electrically insulating tubings inserted between the tubes of the piping lies in the high number of additional parts, which are expensive and make the aircraft still heavier.

One drawback of these insulating joints lies in the need to attach metal braids on the tubes and/or on the connectors to allow electrical continuity between connectors and tubes and with the adjacent structure, so as to discharge the electrostatic charges toward that structure.

One aim of the present invention is to propose a connection device for fluid transmission piping of an aircraft or spacecraft, the device being suitable for connecting two tubes to one another and optionally furthermore to a fluid tank, the device comprising an injection-molded tip that has at least one bent or curved zone and that is made from a composite material with a thermoplastic matrix reinforced by a reinforcing system comprising carbon fibers, the tip having a median longitudinal mold parting plane, which in particular resolves all of the aforementioned drawbacks.

To that end, a connection device according to the invention is such that the carbon fibers extend in an oriented manner (i.e., not random) along the tip, which incorporates mechanical and vibrational stiffening means that are molded to be integral with the tip and extend in said parting plane or symmetrically relative to that plane in said at least one bent or curved zone and/or in the immediate vicinity of that zone.

It will be noted that this thermoplastic tip reinforced by these carbon fibers oriented globally axially simultaneously has high mechanical properties and an electrical conductivity controlled by these fibers (i.e., just necessary to obtain the necessary electrical conductivity to discharge the electrostatic charges in the pipe).

It will also be noted that the tip according to the invention does not penalize the weight or mechanical or vibrational strength of the tubes-tip interfaces. On the contrary, this tip makes it possible to lighten the connection device and therefore the entire pipe incorporating it, such as a fuel pipe, to reduce the assembly time of the parts in the airplane using this reinforcement, and to integrate additional functions, as will be explained below.

It will further be noted that the use of such a connection device essentially made up of this thermoplastic matrix tip was not possible at this time in the aeronautic industry, due to:
excessively high required mechanical properties, in particular the vibrational rigidity,
the impossibility of allowing any creep in the tip, unacceptable to guarantee tightness of the cylindrical links over time, and
the lack of electrical conductivity of thermoplastics.

Indeed, if one chose to increase the electrical conductivity of a thermoplastic by filling it with conductive particles, such as a conductive carbon black, for example, the necessary level of these particles (around 20 to 30%) would be such that the mechanical properties would then become too low to be able to claim the substitution of an aluminum alloy to lighten the tip. If one instead chose to increase the mechanical characteristics of a thermoplastic for example by filling it with short glass fibers, the obtained mechanical characteristics would be too weak to contribute to an aluminum machined in the mass. In short, one of these two properties would be obtained to the detriment of the other.

In summary, the oriented carbon fibers reinforcing the tip according to the invention make it possible to simultaneously obtain the blockage of any creep of the tip, the increased vibrational rigidity able to still further lighten this tip, and the electrical conductivity necessary to discharge the electrostatic charges.

Preferably, said thermoplastic matrix has a base of at least one polymer chosen from the group made up of polyamides such as PA 12, polyaryletherketones (PAEK), polyether ether ketones (PEEK), polyetherketoneketones (PEKK) and their alloys, this matrix having a density preferably lower than or equal to 1.5.

Taking into account the densities and proportions of the aforementioned fibers and using one of these thermoplastic polymers with a density lower than or equal to 1.5, a reinforced and conductive thermoplastic material is obtained with a density of about 1.7+/−0.15, or, for a thickness of 1.4 mm, a surface density lower than 2.4 kg/m$^2$ providing a mass gain of 12%.

According to another feature of the invention, said reinforcing system can be present in the tip according to a mass fraction comprised between 10% and 40%, this system preferably comprising:
said carbon fibers, which preferably have a mean length comprised between 0.5 mm and 3 mm and are chosen in the group consisting of those with an intermediate modulus ("IM") or high modulus ("HM"), and
electrically insulating fibers and/or particles such as glass or aramid fibers, according to a carbon fiber/electrically insulating fibers and/or particles volume ratio comprised between 30% and 80%.

Although "IM" or "HM" carbon fibers are particularly indicated to reinforce the tip according to the invention, it will be noted that the choice of the type and quantity of fibers will be made by adjusting the necessary dielectric conductivity. With the dual constraint of not being too conductive while also being dissipative, the tip must have a resistivity comprised between values of approximately 100 Ohm/m and 100 MOhm·m.

Since one wishes to maximize the reinforcement (i.e., the rigidity and quantity of fibers) without penalizing the weight of the tip and to obtain an intermediate resistivity, a choice will preferably be made to mix the carbon fibers (electrically conductive) and the electrically insulating fibers and/or particles according to the aforementioned ratios.

According to another feature of the invention, said tip can comprise:
two straight portions that extend axially on either side of said at least one bent or curved zone (i.e., n+1 straight portions for n bent or curved zones, with n being an integer 1) and which incorporates said carbon fibers, the majority of which are oriented in the axial direction of a globally cylindrical surface of each portion (i.e., in a non-oblique direction globally parallel to the longitudinal axis of symmetry of each straight portion), and
at least one collar or flange for example fastening the tip to said tank that is also molded to be integral with the tip and that extends radially so as to be adjacent to said at least one bent or curved zone, this collar or flange incorporating said carbon fibers, the majority of which are oriented in the radial direction around the straight portion (i.e., in a direction globally perpendicular to the axis of symmetry of the flange).

It will be noted that these orientation characteristics of the carbon fibers result from in-depth research and design work by the Applicant to obtain a tip that is able to absorb forces without creep (in particular at the permanent force zones, such as the fasteners or attachments) and with an appropriate orientation of the fibers to obtain the targeted rigidity and weight gains. The Applicant has thus managed to identify zones of the tip where the carbon fibers have similar orientations, and the tip therefore has similar mechanical properties. The addition of mechanical and vibrational stiffening means additionally makes it possible to achieve the required characteristics related to the mechanical behavior of the tip.

According to one particular embodiment of the invention, said mechanical and vibrational stiffening means comprise at least one rib or tab that extends in the axial direction of the tip and defines a radial overthickness in said at least one bent or curved zone and/or in the immediate vicinity of the zone.

According to one example of the invention, said mechanical and vibrational stiffening means comprise at least one said rib that extends axially in said parting plane of the tip and that bears on said flange. According to this example of the invention, said at least one bent or curved zone has a curvature for example with a right angle defining an outer surface and an inner surface of the adjacent straight portions that are respectively turned toward the outside and the inside of the curve, said mechanical and vibrational stiffening means comprise a first so-called axial rib forming a radial overthickness on said outer surface and/or a second so-called axial rib forming a radial overthickness on said inner surface.

It will be noted that these ribs or overthicknesses according to the invention can thus be located on the convex side and/or the concave side in the axial "bending" plane of the bent zone (i.e., the mold parting plane), which facilitates stripping without making the molds more complex and further contributes to reducing the mass of the tip.

According to another example of the invention, said mechanical and vibrational stiffening means comprise two said tabs for example in the form of grates that extend symmetrically to one another relative to said parting plane of the tip while bearing on said outer surface of the curve and that are topped by a connecting plate to said tank.

It will be noted that one additional advantage of injection molding a thermoplastic matrix composite to obtain the tip is that it facilitates the addition of the mechanical stiffening means, such as said rib(s) or tabs, at the appropriate locations to obtain the required vibrational rigidity, for example at the base of the fastening lugs or in the zones of the connecting radii, but also to stiffen the bent or curved zone, which, under the background effect of the pressure, works in "unbending".

By decreasing the thicknesses and splining the overstressed zones, it is then possible to consider tip thicknesses of approximately 1.4 mm, for example, to withstand both the required pressures and vibrational rigidities.

Advantageously, the connecting device can further comprise metal fastening members for fastening said flange to said tank, such as screws and/or nuts, which are formed in a single piece by overmolding with fastening lugs of said flange.

In this way, the fastening members and optionally dielectric connecting members are integrated directly into the tip to resolve a quadruple issue:
the need for good electrical contact with the structure,
the creep of the thermoplastic under high stresses,
the difficulty of accessing certain fasteners, and
the reduced assembly time.

Indeed, the sometimes complex shape of the various existing tips or connectors (for example bent at a right angle, or other geometries) can prevent frontal access to the lugs and therefore to the screws or fastening nuts. Yet this overmolding according to the invention of the fastening members advantageously uses injection technique to directly incorporate screws or preferably metal nuts (for repair by retapping), preferably made from titanium or stainless steel to avoid galvanic torques with the carbon fibers contained in the tip of the thermoplastic fastening lugs. This simultaneously resolves the issues of electrical dissipation, creep risks and assembly time.

The injection technology also makes it possible to incorporate fastening inserts faster than by screwing, for example "quarter turn" fasteners, which also make it possible to reduce the assembly time of fuel lines during final assembly, while keeping the same maintenance and electrical contact characteristics.

According to another feature of the invention, the connection device may further comprise, near two ends of said tip intended to receive said tubes, two electrically conductive annular sealing gaskets with a base of at least one elastomer preferably chosen from the group made up of silicone and fluorosilicone rubbers (rubbers that are particularly advantageous for their resistance to fuels, for example filled with carbon black, carbon nanotubes and/or other conductive particles) and that are mounted in contact with a radially inner face of said tip while being attached in two respective circumferential grooves of said tubes or overmolded on those tubes, these joints being able to ensure the electrical continuity of the tubes with the tip and the tank.

It will be noted that each electrically conductive elastomeric joint could not be used with aluminum connection tips, since these require antifriction or anticorrosion treatment that causes their surfaces not to be electrically conductive. In the present invention, this type of joint can be used because each joint is in direct contact with an electrically conductive material that does not have a corrosion risk, and that then makes it possible to ensure the electrical continuity of the tubes with the tip, and furthermore, owing to the fastening lugs of the tip, with the structure of the adjacent fuel tank.

As explained below, one thus obtains the electrostatic discharge in the structure of the aircraft without needing to use additional electrically conductive braids as in the past.

Advantageously, said tip can be provided with no metal circumferential layer.

Also advantageously, said tip can be provided with means for heating the fluid traveling through it that are overmolded on the wall of the tip. The electrical resistivity properties of the part are then used to make it heating, which is particularly interesting when the transported fluids are subject to a risk of freezing (for example, case of long-range planes flying at an outside temperature close to −55° C.). To heat the tip, it may be powered by an electrical connection able to be added by overmolding during injection of the part, having specified that doing without a low current increases the temperature of the tip above the freezing point of the conveyed fluid.

A pipe according to the invention for fluid transmission piping in an aircraft or spacecraft, the pipe in particular being intended to be mounted in each of the composite wings of an airplane to transport a fuel and comprising two tubes that are preferably nonmetallic and are connected to one another via a sliding and rolling link by a connecting device with a thermoplastic matrix composite tip, is characterized in that the connecting device is as previously defined and has no metal connector assembled to the tip for the connection of the latter to the tubes.

Advantageously, the pipe may not have any electrically insulating tubing between the tubes.

Also advantageously, the pipe may be provided with no electrically conductive braid secured to the tip for the electrical connection of the latter to said tubes and said tank, the connection device comprising, near two ends of the tip receiving the tubes, said two electrically conductive annular sealing gaskets that are mounted in contact with a radially inner face of the tip while being attached in two respective circumferential grooves of the tubes or overmolded on these tubes and that ensure the electrical continuity of the tubes with the tip and the tank.

It will be noted that doing without such an additional conductive braid makes it possible to significantly reduce the weight, assembly times and risks of incorrect assembly of the pipes, and therefore to improve the safety of the vehicle equipped with it, such as an aircraft.

A method according to the invention for manufacturing a connection device as previously defined comprises:

a) injection molding the thermoplastic matrix composite tip in separate locations of a mold of said at least one bent or curved zone and said two straight portions that extend axially on either side of that zone, preferably using a rotating core with curved output kinematics, and b) overmolding or welding these two straight portions to this bent or curved zone by means of globally cylindrical steps corresponding to these straight portions.

It will be noted that this method according to the invention makes it possible to provide a solution to the usual problems of thermoplastic tips filled with fibers, which arises at the steps of the joints and for the production of the bent zones (for example at 90°) with no angular point in the inside of the bend, to avoid any pressure loss or cavitation in the flow of the transported fluids. Indeed, to be tight, the steps must be cylindrical and partly smooth, therefore with no weld line or other mold "parting". Yet machining to resolve this, in light of the presence of machined fibers on the surface, would cause premature wear of the joints in terms of endurance and would significantly increase the manufacturing cost of the parts.

One solution to have a bent pipe with perfectly smooth steps without requiring machining could consist of using complex cores, combining "key" drawers with double movement cores (release/retraction) to be able to taper them. However, this solution is expensive in terms of tooling and may be difficult to mechanize due to a bulk of the cylinders or other mechanisms in the mold.

It will, however, be noted that it is possible, as an alternative to this method with two steps a) and b) according to the invention, to manufacture this tip directly, in a single molding step.

DESCRIPTION OF THE DRAWINGS

Other features, advantages and details of the present invention will emerge from reading the following description of several example embodiments of the invention, provided as an example and non-limitingly, the description being done in reference to the appended drawings, in which.

DETAILED DESCRIPTION

Figure 1:
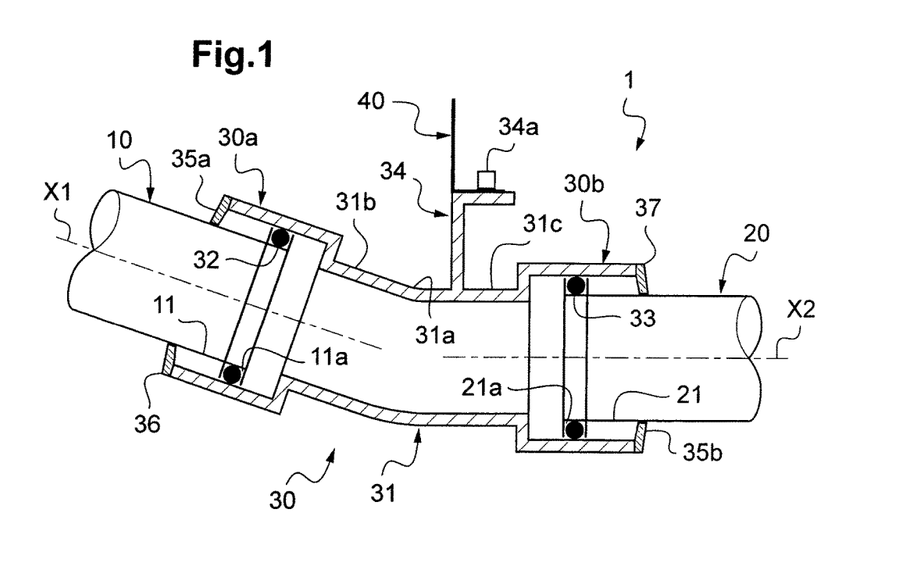
FIG. 1 is a diagrammatic axial sectional view of a pipe according to one example of the invention with a curved tip connected to two tubes and furthermore to an adjacent structure of an aircraft.
Figure 2:
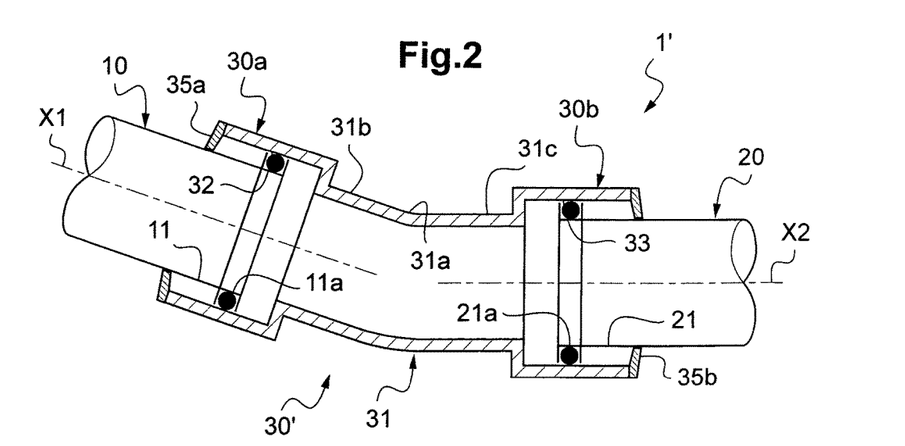
FIG. 2 is a diagrammatic axial sectional view of a pipe according to another example of the invention with a curved tip connected only to two tubes.

A pipe 1, 1' according to the examples of the invention shown in FIGS. 1 and 2 is for example intended to convey an aircraft fuel, and it is made up of two tubes 10, 20 that are preferably nonmetallic and a connection device 30, 30' that connects them to one another directly via sliding and rolling links in two respective end zones 30a and 30b of the device 30, 30', and optionally furthermore connects the tubes 10 and 20 to a fuel tank 40 (see FIG. 1). In both of these cases, this device 30, 30' is made up of an injection-molded tip 31 of the composite type with a thermoplastic matrix having a bent or curved central zone 31a, and two electrically insulating annular sealing gaskets 32 and 33 that are mounted radially between and in contact with two respective end zones 11 and 30a, 21 and 30b of the tubes 10 and 20 and the tip 31.

In general, the tip 31 according to the invention has an axial mold parting plane P (shown in FIGS. 3, 4 and 6), which corresponds to the median longitudinal plane of the tip 31 containing the respective axes of symmetry X1 and X2 of its two straight portions 31b and 31c situated axially on either side of its bent or curved zone 31a.

These conductive joints 32 and 33 ensure the electrical continuity of the tubes 10 and 20 with the tip 31 and optionally with the fuel tank 40 in the example of FIG. 1 by means of a fastening flange 34 for fastening to this tank 40 that is also provided to be conductive, as explained below. More specifically, one can see that each tube 10, 20 is inserted axially and radially inside an end zone 30a, 30b of the tip 31 corresponding to one of its two straight portions 31b and 31c. In these examples, each joint 32, 33 is attached or overmolded in a circumferential groove 11a, 21a of an end zone 11, 21 of the corresponding tube 10, 20. In other words, the tubes 10 and 20 according to FIGS. 1 and 2 are fitted tightly in the two straight portions 31b and 31c of the tip 31 via these joints 32 and 33, which preferably have a base of silicone or fluorosilicone rubber for example filled with carbon black and/or carbon nanotubes.

It is also possible to overmold another electric contact 35a, 35b for example in each of the two ends 36 and 37 of the tip 31. Each of the two contacts 35a, 35b visible in FIGS. 1 and 2 is thus mounted axially below the corresponding joint 32, 33, and it radially connects each tube 10, 20 to the same end 36, 37 of the tip 31 across from that tube 10, 20.

In the example of FIG. 1, the tip 31 according to the invention further incorporates, near its bent zone 31a, the radial flange 34 to fix the tip 31 to a structure of the fuselage or a fuel tank 40 of the aircraft. The flange 34 is formed in a single piece with the tip 31, being integrally molded and ending with electrical grounding means 34*a* at this structure 40.

Figure 4:
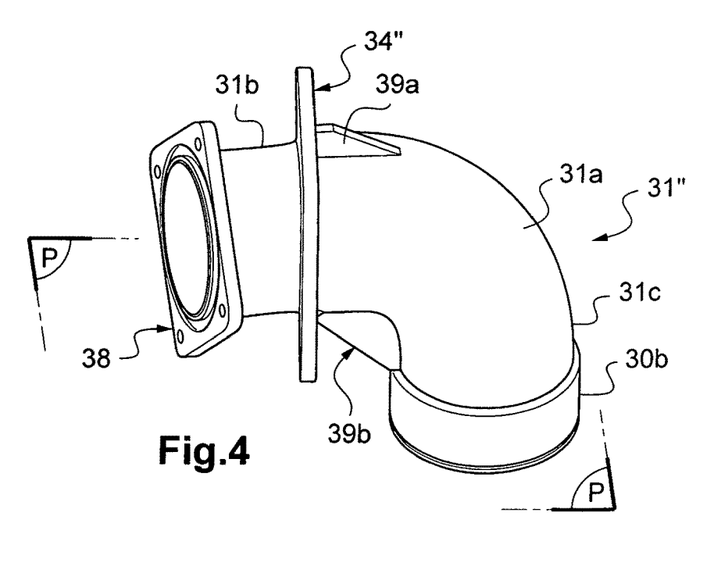
FIG. 4 is a lateral perspective view of a bent tip according to a second example of the invention.

FIG. 4 shows an alternative embodiment according to the invention of a radial fastening flange 34" that here extends over the entire circumference of a straight portion 31*a* of the bent tip 31" and that is for example intended to be fastened to this tank structure 40. Advantageously, the flange 34" is produced by attaching metal fastening members to it for fastening of the tip 31" to the tank 40, such as screws and/or nuts formed in a single piece by overmolding with fastening lugs of the flange 34" (these lugs are visible in the alternative of FIG. 6). As explained above, it will be noted that the use of conductive joints 32 and 33 combined with these fastening members of the tip 31" to the tank 40 makes it possible to do away with any electrically conductive braid connecting the tip 31" to the tubes 10 and 20 and the tank 40.

As shown in FIGS. 3 to 6, one of the ends of the tip 31', 31", 31''' can be provided at its periphery with an auxiliary flange 38 intended for the connection of the tip 31', 31", 31''' to the tube 10, 20 or to a member equipping the pipe 1, 1', such as a pump, for example on the same straight portion 31*b* as that optionally having a flange 34" for fastening to the tank 40 (see FIG. 4). The other end of the tip 31', 31", 31''' axially opposite this auxiliary flange 38 can have a wider zone 30*b* forming a slight end bulge.

The tubes 10 and 20 are for example made from a plastic matrix composite material and, according to the invention, the tip 31, 31', 31", 31''' is injection-molded from a composite material with a thermoplastic matrix reinforced by "IM" or "HM" discontinuous carbon fibers oriented in a globally axial direction and by electrically insulating fibers and/or particles (e.g., glass or aramid). The Applicant has in particular obtained very advantageous results by using, in the tip 31, 31', 31", 31''' according to the invention, intermediate modulus ("IM") carbon fibers in relation with a polyamide-based thermoplastic matrix, in particular a PA12, and high modulus ("HM") carbon fibers in relation with a thermoplastic matrix with a base of a PEEK.

According to the invention, the connection device 30, 30' and the pipe 1, 1' incorporating it have no metal connector assembled to the tip 31, 31', 31", 31''' for the connection of the latter to the tubes 10 and 20, the pipe 1, 1' further having no electrically insulating tubing between the consecutive tubes 10 and 20.

Figures 5, 6, 7:
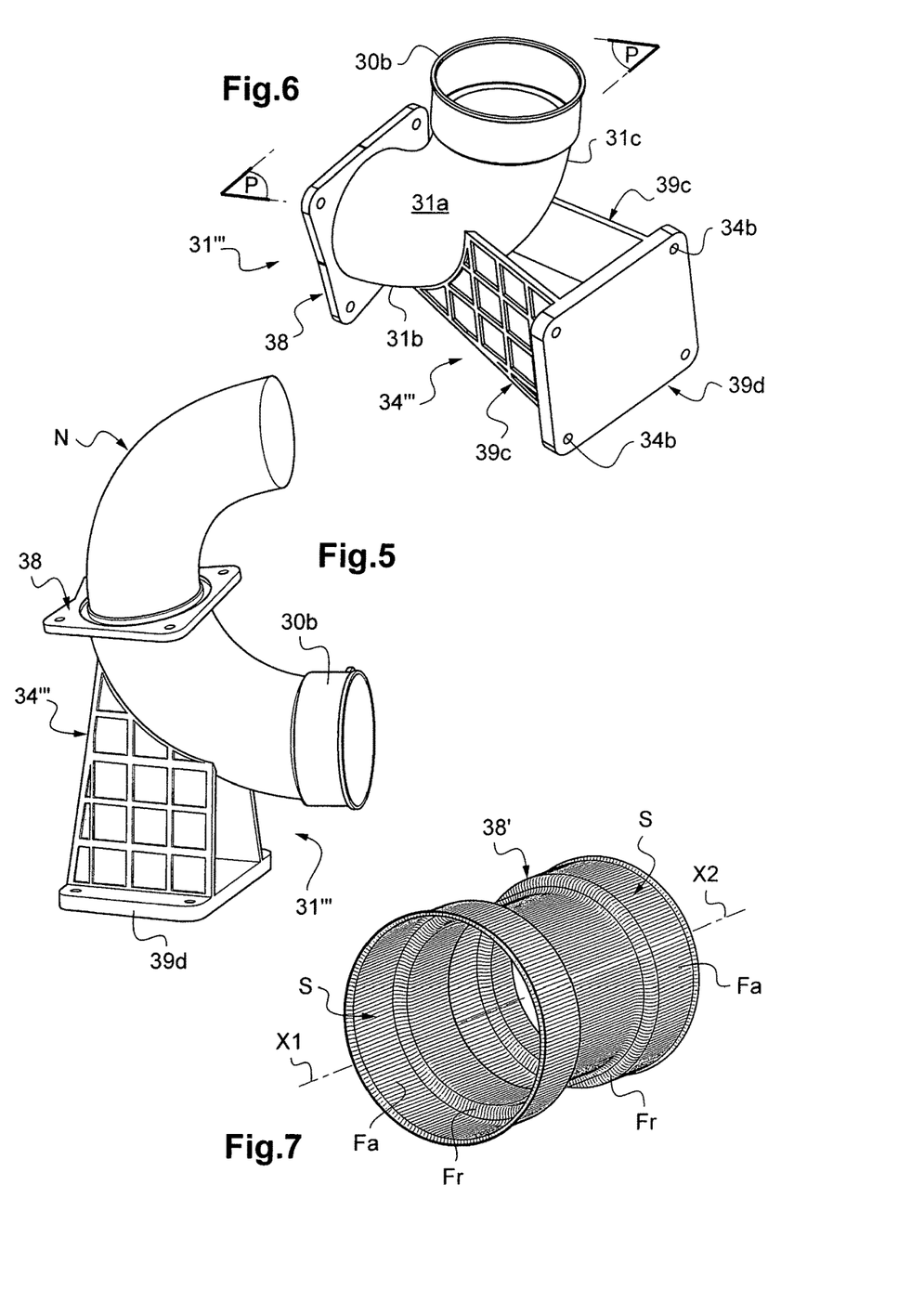
FIG. 5 is a lateral perspective view illustrating the stripping of a bent tip according to a third example of the invention.
FIG. 6 is a bottom perspective view of the bent tip obtained using this method of FIG. 5 according to this third example of the invention.
FIG. 7 is a lateral perspective view of a non-bent tip, but diagrammatically illustrating the orientation of the carbon fibers in a bent or curved tip according to the invention.

FIG. 7 diagrammatically illustrates the orientation of the carbon fibers according to the invention, the majority of which are provided to be axial along each cylindrical surface S (orientation Fa parallel to the longitudinal axis of symmetry X1, X2 of each surface S), and the majority of which are radial on each circumferential collar or flange 38' (orientation Fr perpendicular to X1, X2).

Also according to the invention and in reference to FIGS. 3 to 6, the tip 31, 31', 31", 31''' incorporates means 39, 39*a* and 39*b*, 39*c* suitable for stiffening it from a mechanical and vibrational standpoint that are also molded to be integral with the tip 31, 31', 31", 31''' and are therefore made up of the same material as the rest of the latter (the stiffening means are indeed present on the tip 31 of FIGS. 1 and 2, although they are not visible in this figure since they are outside the axial section chosen for these figures).

Figure 3:
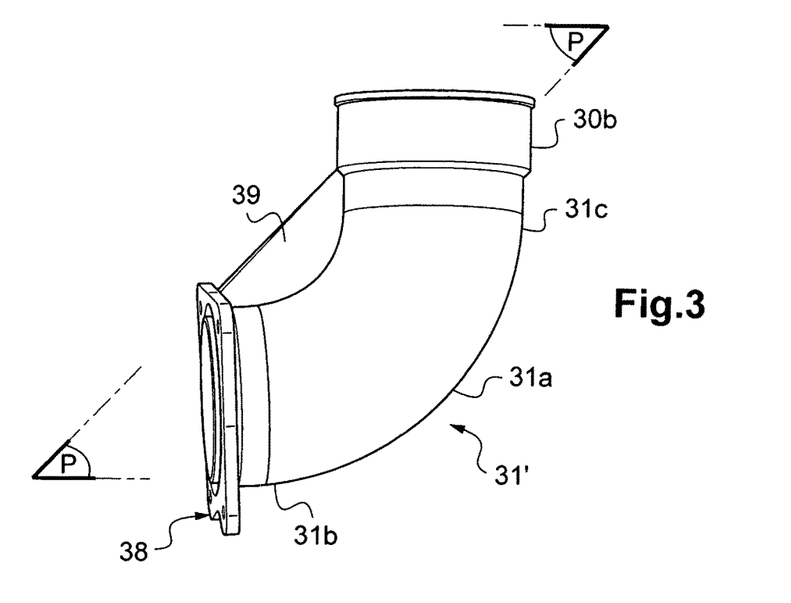
FIG. 3 is a perspective side view of a bent tip according to a first example of the invention.

As illustrated in the first example of FIG. 3, the stiffening means 39 can comprise a rib 39 that extends axially and radially in its bent zone 31*a* in the axial mold parting plane P of the tip 31', on the inner curved surface of this bent zone 31*a*. In this example, this axial rib 39 bears on the one hand on the auxiliary end flange 38 of the tip 31', and on the other hand on the wider end zone 30*b* axially opposite the tip 31'.

As illustrated in the second example of FIG. 4, the stiffening means 39*a* and 39*b* can comprise, in the parting plane P of the tip 31":
 a first substantially trapezoidal axial rib 39*a* on the outer surface of the curve that starts from that surface with an increasing radial height, then bears on the fastening flange 34" of the tip 31" at the tank 40, and
 a second axial rib 39*b* that extends on the inner surface of the curve similarly to the rib 39 of FIG. 3, and bearing, on the one hand, on the fastening flange 34", and on the other hand, just below the wider end zone 30*b* axially opposite the tip 31".

As illustrated in the third example of FIG. 6, the stiffening means 39*c* can comprise, on either side of the parting plane P of the tip 31''', two tabs 39*c* in the form of grates that extends symmetrically relative to one another at that plane P while bearing on the outer surface of the curve and that are topped by a connecting plate 39*d* for connecting to the adjacent structure, such as the fuel tank 40. The plate 39*d* is provided with metal fastening members for fastening the tip 31" to the tank 40, such as screws and/or nuts formed in a single piece by overmolding with fastening lugs 34*b* of the flange 34'''.

FIG. 5 shows a phase of a molding method that can preferably be used to manufacture a tip 31''' not only according to FIG. 6, but generally any bent or curved tip 31, 31', 31" according to the invention. This method essentially consists of separating the or each bent or curved zone 31*a* into two adjacent straight portions 31*b* and 31*c*. This bent or curved zone 31*a* is shaped by a simple, easy-to-implement thermoplastic molding, with a rotating core N of the "saber" type that uses curved output kinematics, to which cylindrical steps are added on each side by thermoplastic overmolding or thermoplastic welding. These steps are then easy to produce without a weld line and with a very small taper, which is acceptable for tightness during operation. It will be noted that the molds used for this method are relatively simple and therefore inexpensive.

The invention claimed is:

1. A connection device for fluid transmission piping of an aircraft or spacecraft, the connection device being suitable for connecting two tubes to one another, the connection device comprising an injection-molded tip that has at least one bent or curved zone and that is made from a composite material comprising a thermoplastic matrix reinforced by a reinforcing system comprising carbon fibers, the injection-molded tip having a median longitudinal mold parting plane, wherein said carbon fibers extend in an axial direction of the molded tip along the injection-molded tip, said injection-molded tip incorporating mechanical and vibrational stiffening means that are molded with the injection molded tip and with said composite material to be integral with the injection-molded tip and extend in said at least one bent or curved zone and/or in the immediate vicinity of that zone, said mechanical and vibrational stiffening means extending in said median longitudinal mold parting plane or symmetrically relative to that median longitudinal mold parting plane and comprising said carbon fibers.

2. The connection device according to claim 1, wherein said injection-molded tip comprises:
 (a) two straight portions that extend axially on either side of said at least one bent or curved zone and which incorporate said carbon fibers, the majority of which are oriented in the axial direction of a globally cylindrical surface of each straight portion; and (b) at least one collar or flange that is also molded to be integral with the injection-molded tip and that extends radially so as to be adjacent to said at least one bent or curved zone, this collar or flange incorporating said carbon fibers, the majority of said carbon fibers are oriented in the radial direction around said straight portion.

3. The connection device according to claim 2, wherein said mechanical and vibrational stiffening means comprise at least one rib or tab that extends in the axial direction of the injection-molded tip and defines a radial overthickness in said at least one bent or curved zone and/or in the immediate vicinity of that zone.

4. The connection device according to claim 3, wherein said mechanical and vibrational stiffening means comprise at least one said rib that extends axially in said parting plane of the injection-molded tip and that bears on said flange.

5. The connection device according to claim 4, wherein said at least one bent or curved zone has a curvature for example with a right angle defining an outer surface and an inner surface of the adjacent straight portions that are respectively turned toward the outside and the inside of a curve, said mechanical and vibrational stiffening means comprising a first so-called axial rib forming a radial overthickness on said outer surface and/or a second so-called axial rib forming a radial overthickness on said inner surface.

6. The connection device according to claim 3, wherein said at least one bent or curved zone has a curvature defining an outer surface and an inner surface of the adjacent straight portions that are respectively turned toward the outside and the inside of the curve, said mechanical and vibrational stiffening means comprising two said tabs that extend symmetrically to one another relative to said parting plane of the injection-molded tip while bearing on said outer surface of the curve and that are topped by a connecting plate to a tank.

7. The connection device according to claim 2, further comprising metal fastening members for fastening said flange to said tank, said metal fastening members are formed in a single piece by overmolding with fastening lugs of said flange.

8. The connection device according to claim 1, wherein said reinforcing system is present in said injection-molded tip according to a mass fraction comprised between 10% and 40%, said reinforcing system comprising:
(a) said carbon fibers, chosen in the group consisting of those with an intermediate modulus or high modulus; and
(b) electrically insulating fibers and/or particles, according to a carbon fiber/electrically insulating fibers and/or particles volume ratio comprised between 30% and 80%.

9. The connection device according to claim 1, wherein said thermoplastic matrix has a base of at least one polymer chosen from the group made up of polyamides, polyaryletherketones, polyether ether ketones, polyetherketoneketones and their alloys.

10. The connection device according to claim 1, wherein it further comprises, near two ends of said injection-molded tip intended to receive said tubes, two electrically conductive annular sealing gaskets with a base of at least one elastomer chosen from the group made up of silicone and fluorosilicone rubbers and that are mounted in contact with a radially inner face of said injection-molded tip while being attached in two respective circumferential grooves of said tubes or overmolded on those tubes, these joints being able to ensure the electrical continuity of the tubes with the injection-molded tip and the tank.

11. The connection device according to claim 10, wherein said injection-molded tip has no metal circumferential layer.

12. A pipe for fluid transmission piping in an aircraft or spacecraft, the pipe being intended to be mounted in each of the composite wings of an airplane to transport a fuel, the pipe comprising two tubes that are connected to one another via a sliding and rolling link by a connecting device with an injection-molded tip, wherein the connecting device the connection device of claim 1 and has no metal connector assembled to the injection-molded tip for the connection of the latter to the tubes.

13. The pipe according to claim 12, wherein the pipe has no electrically insulating tubing between the tubes.

14. The pipe according to claim 12, wherein the pipe has no electrically conductive braid secured to the injection-molded tip for the electrical connection of the latter to said tubes and a tank, the connection device comprising, near two ends of the injection-molded tip receiving the tubes, said two electrically conductive annular sealing gaskets with a base of at least one elastomer chosen from the group made up of silicone and fluorosilicone rubbers and that are mounted in contact with a radially inner face of the injection-molded tip while being attached in two respective circumferential grooves of the tubes or overmolded on these tubes and that ensure the electrical continuity of the tubes with the injection-molded tip and the tank.

15. A method for manufacturing a connection device according to claim 1, wherein the method comprises:
(a) injection molding the injection-molded tip in separate locations of a mold of said at least one bent or curved zone and said two straight portions of the injection-molded tip that extend axially on either side of that zone; and
(b) overmolding or welding the two straight portions to the bent or curved zone by means of globally cylindrical steps corresponding to the straight portions.

16. A connection device for fluid transmission piping of an aircraft or spacecraft, the connection device being suitable for connecting two tubes to one another, the connection device comprising an injection-molded tip that has at least one bent or curved zone and that is made from a composite material with a thermoplastic matrix reinforced by a reinforcing system comprising carbon fibers, the injection-molded tip having a median longitudinal mold parting plane, wherein said injection-molded tip incorporating mechanical and vibrational stiffening means that are molded to be integral with the injection-molded tip and extend in said at least one bent or curved zone and/or in the immediate vicinity of that zone, said mechanical and vibrational stiffening means extending in said median longitudinal mold parting plane or symmetrically relative to that median longitudinal mold parting plane, and wherein said injection-molded tip includes at least one straight portion each having a longitudinal axis of symmetry and each including only carbon fibers which extend in a non-oblique direction globally parallel to said longitudinal axis.

* * * * *